Figure 1:
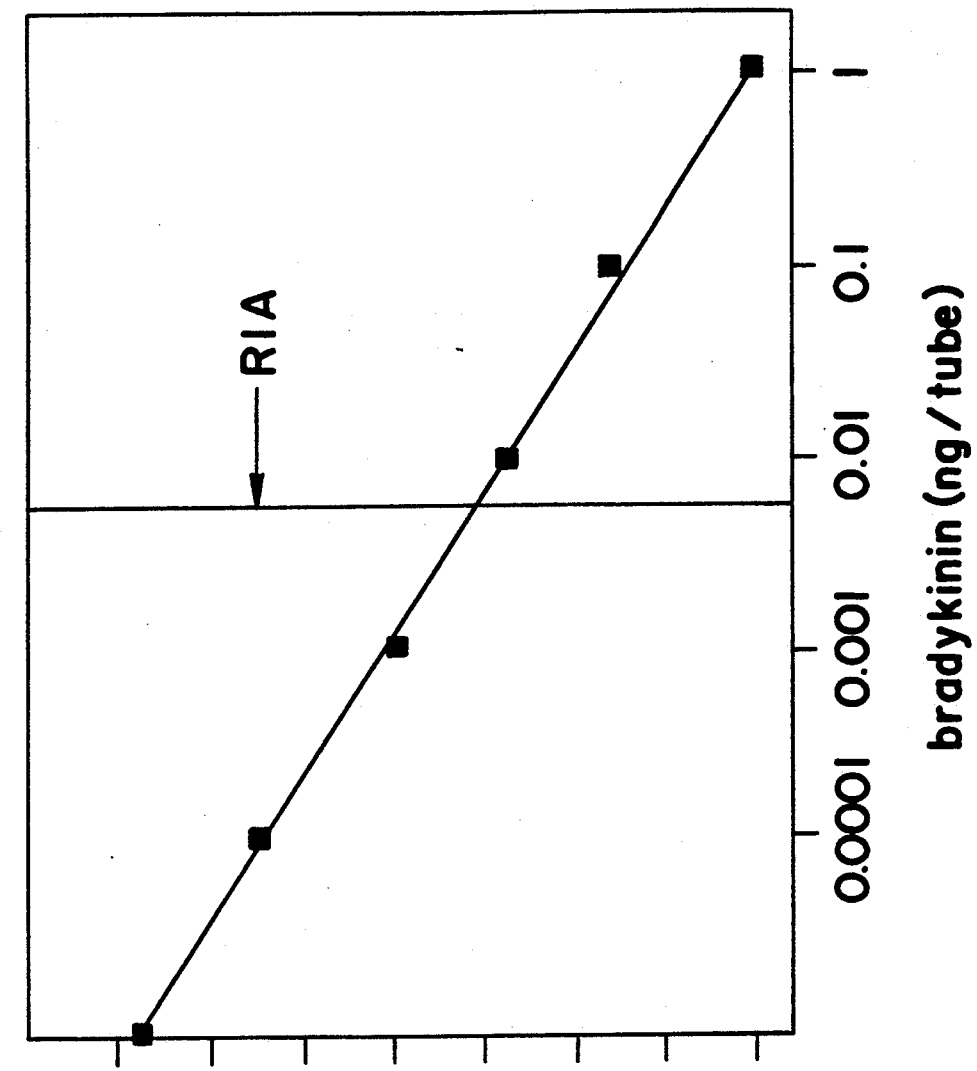

United States Patent [19]

Geiger et al.

[11] Patent Number: 5,098,828

[45] Date of Patent: Mar. 24, 1992

[54] D-LUCIFERIN DERIVATIVES, THEIR APPLICATION AND PROCESSES FOR THE DETECTION OF LIGANDS MARKED WITH AN ENZYME IN THE DETERMINATION OF BIOCHEMICAL SUBSTANCES

[76] Inventors: Reinhard Geiger, Eisenhartstr. 6, D-8000 Munich 60; Werner Miska, Haylerstr. 8, D-8000 Munich 50, both of Fed. Rep. of Germany

[21] Appl. No.: 64,256

[22] PCT Filed: Oct. 24, 1986

[86] PCT No.: PCT/EP86/00615

§ 371 Date: Aug. 18, 1987

§ 102(e) Date: Aug. 18, 1987

[87] PCT Pub. No.: WO87/02667

PCT Pub. Date: May 7, 1987

[30] Foreign Application Priority Data

Oct. 24, 1985 [DE] Fed. Rep. of Germany ..... 35378778

[51] Int. Cl.[5] .................. G01N 33/58; C07F 9/38; C07D 417/04
[52] U.S. Cl. .................................. 435/7.72; 435/8; 536/4.1; 536/17.4; 548/114; 548/178
[58] Field of Search ............ 435/7, 8, 14, 15, 18, 435/19, 21-24, 6, 7.72; 548/114, 178; 530/802, 300; 536/4.1, 17.1, 17.3, 17.4, 27, 29

[56] References Cited

U.S. PATENT DOCUMENTS

| | | | |
|---|---|---|---|
| 4,380,580 | 4/1983 | Boguslaski et al. | 435/7 |
| 4,478,817 | 10/1984 | Campbell et al. | 435/7 |
| 4,649,108 | 3/1987 | Blair | 435/22 |
| 4,665,022 | 5/1987 | Schaeffer et al. | 435/7 |

OTHER PUBLICATIONS

Molecular and Cellular Probes, Reinhard Geiger et al, "New, bioluminescence-enhanced detection systems for use in enzyme activity test, enzyme immunoassays, protein blotting and nucleic acid hybridization", 1989, pp. 309-328, vol. 3.
Journal of Organic Chemistry, vol. 30, No. 7, Jul. 1965, E. H. White et al., "Analogs of firefly luciferin", 2344, 2345, 2347.
Biochemistry, vol. 9, No. 5, Mar. 1970, M. J. Cormier et al, "Studies on the bioluminescence . . . ", 1184–1189.
Chemical Abstracts, vol. 58, No. 4, Feb. 18, 1963, H. H. Seliger et al, "Chemiluminescence of firefly luciferin . . . ".
Journal of the American Chemical Society, vol. 102, No. 9, Apr. 23, 1980, E. H. White et al., "Chemi- and bioluminescence . . . ", 3204.
Biochimica and Biophysica Acta, 256 (1972), 638–644.
Bowie, "Methods in Enzymology", vol. LVII, edited by M. Deluca, Academic Press, NY 1978, pp. 15 & 25–28.
Seliger et al., Science 138, 683–5, 1962.

Primary Examiner—Mary E. Ccperley
Attorney, Agent, or Firm—Bacon & Thomas

[57] ABSTRACT

The object of the invention consists of D-luciferin derivatives of General Formula (I)

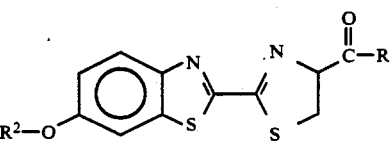

wherein
$R^1$ = OH, alkoxy, alkenyloxy, amino acid, $NH_2$ or oligopeptide and
$R^2$ = H; $H_2PO_3$—; $HSO_3$—; alkyl or alkenyl, optionally substituted by phenyl; aryl;

with $R^3$ = alkyl or alkenyl, optionally substituted by phenyl; mono- or disaccharide or nucleotide.

An object of the invention is further the use of said luciferin derivatives for the detection of ligands in the determination of biochemical substances, in particular in enzyme immuno assays, in blot processes and in nucleic acid hybridization. These ligands are attached to an enzyme (enzyme conjugate). In the process, for example an antigen, a hapten or an antibody is conjugated with an enzyme. The enzyme conjugate is capable of releasing luciferin from the luciferin derivative. The luciferin released is reacted with luciferase. The amount of light emitted in the process is determined. From the data obtained in this manner, the quantity of the substances to be determined may be derived.

5 Claims, 3 Drawing Sheets

Curve for the binding of Bradykinin in competitive solid phase Bioluminescense Enzyme Immunoassay (BEIA)

RIA = Radioimmunoassay; at present limit of detection

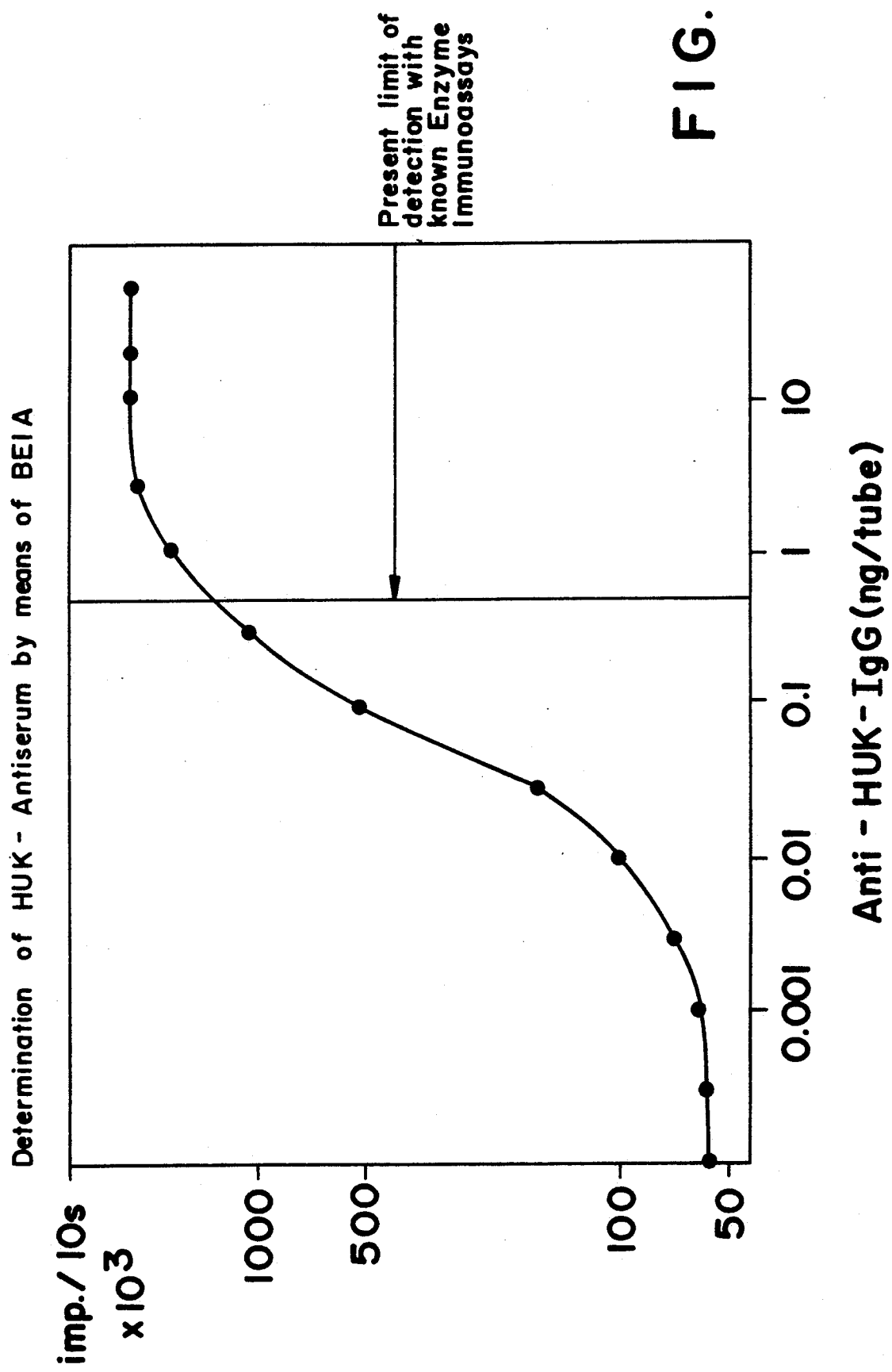

D-LUCIFERIN DERIVATIVES, THEIR APPLICATION AND PROCESSES FOR THE DETECTION OF LIGANDS MARKED WITH AN ENZYME IN THE DETERMINATION OF BIOCHEMICAL SUBSTANCES

The invention concerns D-luciferin derivatives, their application and processes for the detection of ligands marked with an enzyme in the determination of substances, in particular biochemically active substances.

The determination of substances which play a role in biological processes, are biologically active, occur in biological processes, etc., constitutes a significant problem.

Thus, for example, in the field of immunology the determination of antigens, haptens or antibodies is extremely important.

The development of the first radio immuno assays suitable for use in the determination of antigens or antibodies of this type was originated more than 20 years ago. Since then, various immunological methods were developed, in which marked reagents (tracers) are used for the determination of antigens or antibodies.

Enzyme immuno assays, in which enzymes serve as markers, are of particular importance. Enzyme immuno assays of this type are being employed increasingly compared to radio-immuno assays, as there is no radioactive waste, the reagents may be stored longer and the tracer is not destroyed.

Enzyme immuno assays are divided into homogeneous (homogeneous enzyme assays; EMIT) and heterogeneous (heterogeneous enzyme immuno assays; ELISA).

A review of the most important methods of such enzyme immuno assays may be found in:

J. Clin. Chem. Clin. Biochem., Vol. 18, 1980, pages 197-208, "Enzyme immuno assays in clinical chemistry: present status and trends" by M Oellerich and "Principles of Enzyme Immuno Assays" by M. Oellerich in "Methods of Enzymatic Analysis", Vol. 1, H. U. Bergmeyer, ed., p. 233-260, Verlag Chemie, Weinheim/Bergstrasse (1983).

A summary article concerning the possible applications of enzymes in immuno assay methods is found in:

Analyst, May 1984, Vol. 109, pages 533-547, "Use of Enzymes in Immuno Assay Techniques, a Review" by Christopher Blake and Barry J. Gould.

In the case of immuno assays of this type enzymes serve as markers. In the process, the enzymes combine with a ligand into a ligand-enzyme conjugate. The ligand may be an antibody, an antigen or a hapten. The ligand marked by an enzyme (for example an antibody marked with an enzyme) is then reacted with its biochemical "counter part" (for example an antigen), wherein the ligand is added to its biochemical counter part.

For the detection of ligand-enzyme conjugates, they are reacted with a substrate. The enzymes release a reaction product from the substrate, which may be detected analytically, for example by photometry, potentiometry, thermometry or by scintillation spectrometry.

In these enzyme immuno assays therefore the amplification effect by way of the substrate reaction of the enzymes per unit time is utilized. It is possible in this manner to determine quantitatively the amount of the reaction product formed and thus also the quantity of bound ligands marked by an enzyme (antibody, antigen, hapten).

The quality of an enzyme immuno assay thus depends among others on the amplification effect and the limit of detection relative to the reaction product.

Frequently, however, such enzyme immuno assays are not sensitive enough. This may be the result of the fact that the amplification effect is not sufficiently large in the substrate reaction or that the limit of detection for the reaction product is too high.

It has now been discovered surprisingly that luciferin derivatives may be used as substrates for the detection of ligands marked by enzymes. The enzyme releases the luciferin compound from the derivatives, which in turn may be again reacted with an enzyme, i.e. the luciferase of the fire-fly Photinus pyralis with the emittance of light. From the amount of light emitted in the process the amount of the ligand-enzyme conjugate may be determined quantitatively, from which in turn the quantity of the substance to be determined may be calculated.

It is therefore the object of the present invention to provide compounds used in the process.

This object is attained by the formation of D-luciferin derivatives of the following general formula (I):

$$R^2-O-\underset{}{\text{(benzothiazole)}}-N=\underset{S}{\overset{}{\text{(thiazoline)}}}-\overset{O}{\underset{}{\overset{\|}{C}}}-R^1 \quad (I)$$

wherein
- $R^1$ signifies a hydroxy or amino group, a linear or branched $C_1$–$C_{20}$ alkoxy or $C_2$–$C_{20}$ alkenyloxy group, an L-amino acid radical, bonded by means of the α-amino group, or an oligopeptide radical with up to 10 L-amino acid units attached by means of the α-amino group of the terminal amino acid units, and
- $R^2$ is a hydrogen atom, a $H_2PO_3$ or $HSO_3$ group, a linear or branched $C_1$–$C_{20}$ alkyl or $C_2$–$C_{20}$ alkenyl group, optionally substituted by one of more phenyl radicals, an aryl group with 6 to 18 C atoms, a group of the general formula (II)

$$R^3-\overset{O}{\underset{}{\overset{\|}{C}}}- \quad (II)$$

wherein
- $R^3$ is a linear or branched $C_1$–$C_{20}$ alkyl or $C_2$–$C_{20}$ alkenyl group, optionally substituted with a phenyl radical, or a $C_6$–$C_{18}$ aryl group, a naturally occurring nucleotide radical with 1 to 3 phosphate groups attached by means of the phosphate group or groups, or
- a glycosidically attached mono- or disaccharide, with the exception of D-luciferin or D-luciferin methyl ester.

The alkyl or alkoxy groups of the radicals $R^1$, $R^2$ and $R^3$ in particular are those with 1 to 8, preferably 1 to 6 and even more preferably 1 to 4 carbon atoms.

The alkenyloxy or alkenyl groups of the substituents $R^1$, $R^2$ and $R^3$ have in particular 2 to 8, preferably 2 to 6 and even more preferably 2 to 4 carbon atoms.

As the L-amino acid radicals preferably those of naturally occurring amino acids. The oligopeptide is preferably built of these naturally occurring amino acids.

The aryl groups are for example phenyl or naphthyl groups. The monosaccharide consist for example of a galactose, glucose, manose or fucose radical.

The following compounds may be used as the nucleotides: adenosine, guanosine, thymidine, cytidine or uridine mono-, di- or tri-phosphate.

The compounds according to the invention of General Formula (I) and luciferin methyl ester may be used as substrates for the detection of ligands to which an enzyme is attached. The enzyme must be capable of releasing from the aforementioned luciferin derivatives the compound luciferin. The luciferin released is detectable even in the slightest concentration by means of the enzyme luciferase of the fire-fly Photinus pyralis.

In this manner therefore all ligands to which a corresponding enzyme is attached, may be detected.

It is the function of a ligand to become added to a biochemical substance corresponding to said ligand ("biochemical counter part") or to form a complex with it. Following this conversion, the combination of the marked ligand and the biochemical counter part is reacted with a luciferin derivative (substrate), as described below in more detail. The quantity of the "combination" may be calculated from the substrate converted, from which in turn the quantity of the substance to be determined may be derived.

The substance to be determined may consist for example of the aforementioned biochemical counter part. But it may also be the ligand itself, if a marked ligand is made to compete with an unmarked ligand of unknown concentration for the same biochemical counter part.

It is further possible that neither the aforementioned biochemical counter part nor the ligand represents the substance to be determined, but a substance capable of being added to the biochemical counter part. In this process the substance to be determined is attached to the ligand by means of an intermediate element (for example probe, sonde, second antibody) representing the said biochemical counter part.

The luciferin derivatives thus represent a new class of substrates to be used in tests wherein ligands marked with an enzyme are employed.

A further object of the invention is therefore a process for the detection of ligands in the determination of biochemically active substances, wherein the ligand is marked with an enzyme while forming a ligand-enzyme conjugate. This process is characterized in that an enzyme is used, which is capable of releasing luciferin from the luciferin derivatives of General Formula (I) or from luciferin methyl ester, with the aid of the enzyme conjugate, that the luciferin released is reacted with the enzyme luciferase of the fire-fly Photinos pyralis, the amount of light emitted determined quantitatively, in particular luminometrically, and the quantity of the substance to be detected, determined.

The process according to the invention is applicable in particular to immuno assays. These immuno assays are carried out in a known manner with the use of antibodies, haptens or antigens, to which an enzyme is attached. Detection is effected as follows. Luciferin is released by means of the enzyme conjugate from the luciferin conjugate, the luciferin released reacted with the abovespecified enzyme luciferase, the amount emitted determined quantitatively, in particular luminometrically, and the amount of the antigen, antibody or hapten determined from the data obtained.

In the immuno assay according to the invention an enzyme is conjugated in a manner known in itself with a ligand (antibody, antigen or hapten). These ligands may consist of the type of biochemically active substances that is to be determined. This case will be explained as an example in a competitive immuno assay.

Such competitive immuno assays may be used for example for the determination of antigens. For this purpose, a known amount of the antigen is combined with the marker enzyme. This enzyme marked antigen, the quantity of which is known, is reacted together with a sample of the same antigen, which is not marked and the unknown quantity whereof is to be determined, with a limited, predetermined amount of corresponding antibodies. In the process the marked and unmarked antigens compete for the numerically limited "antibody places". The smaller the quantity of the unmarked antigens to be determined, the more of the antigens marked with an enzyme are bound to the antibodies.

The antibodies may be attached to a solid carrier. Following the above described reaction, the other reactants are removed, for example by simple rinsing. This leaves the carrier with the antibodies attached thereto, to which the antigens (in this example these are both marked and unmarked) are bound or added. The quantity of the marked antigens bound to the antibodies is determined by means of the luciferin derivatives. The amount of unmarked antigens may be calculated from it. In this case the ligand represents the type of biochemically active substance that is to be determined.

It is, however, also possible to conjugate the enzyme with a ligand that itself is not to be determined. This signifies that the marked ligand does not represent the type of biochemically active substance that is to be determined. Rather, the marked ligand is reacted with the corresponding biochemical counter part that is to be determined. In this manner, information concerning the aforementioned counter part is obtained by means of the marked ligands.

However, the application of the aforedescribed mode of detection by means of luciferin derivatives is not restricted to enzyme immuno assays. Rather, the compounds according to the invention of General Formula (I) together with luciferin methyl ester, may also be used as substrates in detection by the blot method (Western blot) and in nucleic acid hybridization.

The detection system according to the invention may be used generally for the detection of ligands that may be marked with an appropriate enzyme and which are capable of reacting with a corresponding biochemical substance by addition. It is possible in the process to utilize additional intermediate elements, in order to bond the biochemical substance to be determined to the ligand. Thus, an appropriate intermediate element may be attached to the biochemical substance, wherein the intermediate element is capable of entering an addition bond with the ligand.

The enzyme conjugates to be used in the enzyme immuno assays may be prepared by known methods, which are described for example in the following references:

J. Carlsson et al., Biochem. J. 173, 723-737 (1978) and H. Tae, Meth. Enzymol. 91, 580-609 (1983).

As the enzymes, according to the invention, those capable of releasing from a luciferin derivative, including luciferin methyl ester, the luciferin compound.

The following may be cited as suitable enzymes:

amidases, aminocyclase I, esterases, carboxypeptidase A and B, kininase II, arylsulfatase, alkaline and acid phosphatases, lipases, acetylesterase, nucleotidases, phospholipase A-D, α- and β-glucosidases, α- and β-amylases and nucleases.

Thus, for example carboxylesterase (EC 3.1.1.1) [EC=Enzyme Comission (System) of the International Union for Biochemistry] splits the compounds of General Formula (I), wherein $R^2$ signifies a hydrogen atom and $R^1$ an alkenyl or alkoxy group, into luciferin and alcohol. For example, from luciferin methyl ester, luciferin and methyl alcohol are formed.

Carboxypeptidase A (EC 3.4.17.1) splits the luciferin derivatives of General Formula (I), wherein $R^2$ is a hydrogen atom and $R^1$ an amino acid, into luciferin and the corresponding amino acid. Thus, for example, from luciferylphenylalanine, luciferylglycine or luciferylmethionine, luciferin is formed together with phenylalanine, glycine or methionine.

Carboxypeptidase A in this process is nonspecific relative to the amino acid.

Carboxypeptidase B (EC 3.4.17.2) splits compounds of General Formula (I) wherein $R^2$ is a hydrogen atom and $R^1$ arginine or lysine. Luciferin and arginine or lysine are formed in the process.

α- and β-amylases (EC 3.2.1.1 and EC 3.2.1.2) split the compounds of General Formula (I), wherein $R^1$ is a hydroxy group and $R^2$ a disaccharide, into the corresponding disaccharide and luciferin.

Kininase II (EC 3.4.151) splits the compounds of General Formula (I), wherein $R^2$ is a hydrogen atom and $R^1$ a dipeptide, into the corresponding peptide and luciferin. If $R^1$ represents other oligopeptides, microbial proteinases are used (EC 3.421.14 or EC 3.4.22.-). Lipases (EC 3.1.1.-) split the compounds of General Formula (I), wherein $R^1$ is a hydroxy group and $R^2$ a

radical, into the corresponding acid and luciferin.

Nucleotidases (EC 3.1.3.-) and nucleases split the compounds of General Formula (I), wherein $R^1$ is a hydroxy group and $R^2$ a nucleotide, into the corresponding nucleotide and luciferin.

Acetylesterase (EC 3.1.1.6) splits the compounds of General Formula (I), wherein $R^1$ is a hydroxy group and $R^2$ a $CH_3$—CO radical, into acetic acid and luciferin. Amidases split luciferin amide into luciferin and ammonia. Aminoacylase splits luciferyl amino acids into luciferin and the corresponding amino acid.

Arylsulfatase (EC 3.1.6.1) splits the compounds of General Formula (I), wherein $R^1$ is a hydroxy group and $R^2$ a $HSO_3$ group, into luciferin and $H_2SO_4$.

Alkaline and acid phosphatase (EC 3.1.3.1) split the compounds of General Formula (I), wherein $R^1$ is a hydroxy group and $R^2$ a $H_2PO_3$ group, into luciferin and $H_3PO_4$.

α/β-glucosidases (EC 3.2.1.20 and EC 3.2.1.21) split the compounds of General Formula (I), wherein $R^1$ is a hydroxy group and $R^2$ a glucose radical, into the corresponding α/β-glucose and luciferin.

If in the immuno assay according to the invention compounds of General Formula (I), wherein $R^1$ is a radical other than a hydroxy group and $R^2$ a radical other than a hydrogen atom, then two of the aforementioned enzymes must be used to release luciferin from the derivate.

It is thus possible with the abovedescribed enzymes to release from a luciferin derivative, including luciferin methyl ester, luciferin. The compounds used according to the invention thus serve as substrates for the detection of ligands marked with enzymes. Ligands of this type marked with enzymes may be used in highly varied fields of application, for example in immuno assays.

The luciferin released is detectable even in the smallest concentration with the enzyme luciferase of the fire-fly Photinus pyralis.

In the conversion of luciferin with the luciferase enzyme the following reaction is taking place:

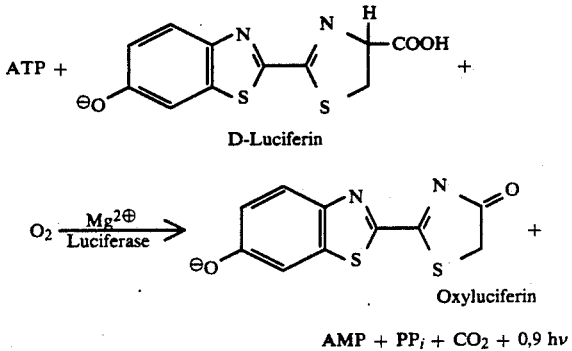

ATP is consumed in this reaction. Photons with a wave length of 562 nm are emitted. Biolumiscence is therefore present. The light emitted is determined luminometrically.

Details of the abovedescribed reaction are known and are described among others in:

Luminometry by K. Wulff in Methods of Enzymatic Analysis, Vol. 1 (H. U. Bergmeyer, Editor), pages 340–368, Verlag Chemie, Weinheim, Bergstrasse (1983).

The reaction of the luciferin with luciferase increases the sensitivity of the detection of marked ligands. This signifies in other words that an improved detection system is provided by the invention.

According to the invention, therefore enzymes capable of releasing luciferin from a luciferin derivative are used as markers. These enzymes may be conjugated with the ligand in question, which may consist of antibodies, antigens, haptens, etc., by known processes.

These marker enzymes may be used in all of the known enzyme immuno assays, for example those mentioned above, whether they are homogeneous or heterogeneous enzyme immuno assays.

The luciferin obtained by the reaction of these enzyme conjugates with luciferin derivatives is determined by means of bioluminescence with the aid of luciferase.

The compounds according to the invention and the immuno assays may be used in clinical chemistry for the determination of antibodies and antigens (hormones [TSH, tyroxin, $T_3$, $T_4$], peptides, proteins, etc.), in environmental analysis (immunological determination of toxic substances [plant protective agents, etc.]), prostaglandins, thromboxanes, monoclonal antibodies, in food chemistry and in all immunological investigation methods.

The detection system according to the invention may be utilized further in the blot process and in nucleic acid hybridization.

The compounds according to the invention may be prepared in the following manner.

The compounds of General Formula (I), wherein $R^2$ is a hydrogen atom and $R^1$ an alkoxy group, may be prepared by reacting luciferin with a corresponding alcohol ($R^1$—H) in the presence of dicyclohexylcarboxydiimide in DMF.

The compounds of General Formula (I), wherein $R^2$ is a hydrogen atom and $R^1$ an amino acid or an oligopeptide, may be prepared by reacting D-luciferin-hydroxysuccinic imide ester (Example 1) with the corresponding amino ester or the corresponding oligopeptide.

The compounds of General Formula (I) wherein $R^1$ is a hydroxy group and $R^2$ an alkyl or alkenyl group, optionally substituted with one or several phenyl residues, may be prepared as follows:

Luciferin is reacted with diazomethane and a compound of Formula (I) is obtained, wherein $R^1$ is a methoxy group. This compound is reacted with an alkyl chloride (for example butyl chloride) or alkenyl chloride to obtain compounds of General Formula (I), wherein $R^2$ is a $C_1$–$C_{20}$ alkyl group or a $C_2$–$C_{20}$ alkenyl group. Subsequently, the methyl group is split off from $R_1$ enzymatically with carboxyesterase, whereby a compound of General Formula (I) is obtained, wherein $R^1$ is a hydroxy group.

The compounds according to the invention of General Formula (I) wherein $R^2$ is an aryl group, are obtained in a similar manner.

To prepare the compounds of General Formula (I) wherein $R^1$ is a hydroxy group and $R^2$ a group of General Formula (II)

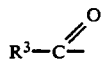

is again obtained in an analogous manner. However, the corresponding acid chlorides are used.

In the synthesis of compounds of General Formula (I), wherein $R^2$ is a mono- or disaccharide adical and $R^1$ represents a hydroxy group, the initial material is again luciferin. After protecting the carboxyl group ($R^1$=OCH$_3$), this protected compound is reacted with $^1$Br-mono or disaccharides and subsequently the methyl group of the $R^1$ radical cleaved off with carboxylesterase.

The compounds according to the invention in which $R^1$ is a hydroxy group and $R^2$ a nucleotide radical, are obtained by the following reaction diagram:

SCHEME

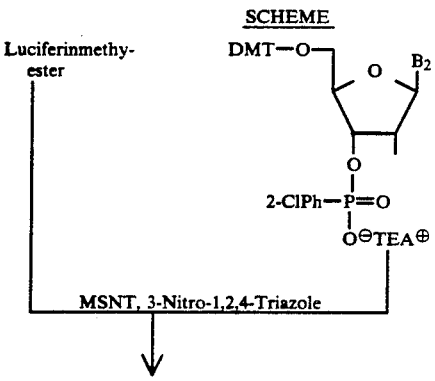

-continued
SCHEME

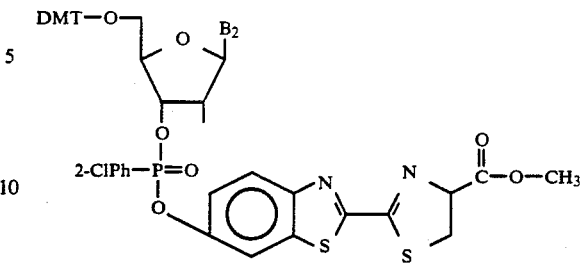

In the scheme:
B$_2$=an optionally protected base;
DMT=4,4'-dimethoxytrityl;
TEA=triethylammonium;
MSNT=1(mesitylene-2-sulfonyl)-3-nitro-1,2,4-triazole;
2-ClPh=2-chlorophenyl.

This synthesis thus begins with luciferin methyl ester. The latter is reacted according to the above diagram with a protected nucleotide, for example in DMF. It is possible to use not only nucleotides with one phosphate group, but also those with two or three phosphate groups, i.e. the corresponding di- or triphosphates.

The protective groups are split off the compound obtained in a known manner and, if so desired, the methyl group is removed with esterase, so that a compound according to the invention, with $R^1$=OH is obtained.

As a protected nucleotide, for example N$^6$-benzoyl-5'-O(4,4'-dimethoxytrityl)-2'-deoxyadenosine-3'-(2-chlorophenyl)-phosphate may be used. Compounds are used further in which the 2'-deoxyadenosine group is replaced by a 2'-deoxyguanisine, 2'-deoxy-thymidine, 2'-deoxyuridine, 2'-deoxycytidine, 2'-guanisine, 2'-adenosine, 2'-cytidine, 2'-thymidine or 2'-uridine group.

In keeping with the above scheme, it is also possible to obtain compounds according to the invention, in which $R^1$ is a $C_{1-20}$-alkoxy or a $C_{2-20}$-alkenyloxy group. The initial material then is not methyl ester, but the corresponding ester.

An alkenyl group is defined in the present application as an aliphatic hydrocarbon radical, containing one or several double bonds, for example vinyl, allyl, propenyl, butenyl. An alkenyloxy group is an alkenyl group bonded by means of an oxygen atom.

To prepare the luciferin derivatives according to the invention wherein $R^1$ is an amino acid radical or an oligopeptide and $R^2$ a nucleotide, the process begins with luciferin derivatives in which $R^1$ is an amino acid radical or an oligopeptide. Subsequently, the functional groups of the $R^1$ residue are protected in a manner known in itself and the reaction is effected as indicated in the diagram To prepare the luciferin derivatives according to the invention wherein $R^1$ is an alkyl or alkenyl radical and $R^2$ has the aforecited significance, but does not represent a nucleotide radical, initially the $R^1$ residue is introduced, followed by the $R^2$ residue. The process is as described in the introduction. A similar process is followed when $R^1$ is an amino acid radical or an oligopeptide. It is, however, convenient to protect the functional groups of the $R^1$ radical prior to the introduction of the $R^2$ radical in a manner known in itself. These protective groups are then split off following the introduction of the $R^2$ radical.

The compound in which $R^1$ is an amino group and $R^2$ a hydrogen atom, is prepared by reacting luciferin hydroxysuccinic imide ester with ammonia.

The aforecited reactions are carried out conveniently in an inert organic solvent, such as THF, dioxane, pyridine or DMF. Purification may be carried out by HPLC.

The invention will become more apparent from the following examples:

The following buffers are used in these examples:

A: 0.015 mole/l $Na_2CO_3$ pH 9.5

B: 0.01 mole/l $K_2HPO_4$, 0.015 mole/l NaCl, 0.005% Tween 20, pH 7.4

C: 2.7 mmole/l $KH_2PO_4$, 6.5 mmole/l $Na_2HPO_4$, 0.137 mole/l NaCl, 0.05% Tween 20, pH 7.4 (prior to use, 0.1% cattle serum albumin is added).

IMMUNO ASSAYS EXAMPLES

EXAMPLE A

Assay for Peptide Determination, Demonstrated on Bradykinin

An antibradykinin immuno globulin solution (30 µg/ml buffer A) is introduced into the depressions of a microtiter plate and incubated overnight at 4° C. It is obtained in this manner that the antibradykinin immuno globulin is "absorbed" on the microtiter plate. It is then washed five times with the buffer B.

Subsequently, 0.1 ml of a bradykinin-carboxylesterase conjugate (50 µ/ml buffer C) and 0.1 ml of a bradykinin solution in various concentrations (bradykinin is also dissolved in the buffer C), are introduced into the depressions of the microtiter plate and incubated overnight at 4° C. In the process the bradykinin enzyme (esterase) conjugate and the pure bradykinin compete for the anti-bradykinine, immuno globulin. The higher the concentration of the pure bradykinin, the less of the bradykinin enzyme conjugate will be bound to the antibradykinin immuno globulin. This constitutes a competitive heterogeneous enzyme immuno assay in which the antibody is bound to a solid phase.

Subsequently, the plate is washed five times with the buffer B.

Into the depressions of the microtiter plate then 0.2 ml of a luciferin methyl ester ($2 \times 10^{-6}$ mole/l in 50 mmole/l tris/HCl; pH 7.5) are introduced and incubated for 1 hour at 37° C. (Detection system I).

Subsequently, 0.1 ml is taken from each of the depressions and added to 0.4 ml of a "bioluminescence cocktail". This "bioluminescence cocktail" is composed as follows:

---
30 mmole/l HEPES (N-2-hydroxyethylpiperazine-N'-2-ethanesulfonic acid
6 mmole/l $MgCl_2$
6 mmole/l ATP
0.5 mmole/l ETDA
80 µmole/l DTT (dithiothreitol)
1 µg luciferase (of the fire-fly *Photinus pyralis*)
Total volume: 0.4 ml; pH 7.75
---

The light pulses are then measured for 10 sec.

The data obtained are correlated with the bradykinin used in different concentration and a standard curve, shown in FIG. 1, is plotted.

If it is now desired to determine an unknown bradykinin concentration, the immuno assay described above is carried out, the light pulses measured for 10 sec and the unknown bradykinin concentration determined from the data together with the standard curve.

As seen in FIG. 1, it is possible to determine with the immuno assay according to the invention, bradykinin in concentrations down to $2 \times 10^{-13}$ [g/cavity].

This is significantly more sensitive than the radio immuno assay used heretofore for the determination of kinins in urine. In this known radio immuno assay antiserum was used against synthetic bradykinin in combination with marked tyr[8]-bradykinin. This known assay is capable of detecting bradykinin only to a concentration of $10^{-11}$ [g/cavity]. Details relative to this known radio immuno assay may be found in: Journal of Laboratory and Clinical Medicine, Vol. 91, 5, pages 721–728, May 1978 "A Sensitive Radioimmunoassay Method for Urinary Kinins in Man".

It is possible to use in the conjugate in place of carboxylesterase, carbopeptidase A (EC 3.4.17.1), carboxypeptidase B (EC 3.4.17.2), arylsulfatase (EC 3.1.6.1) or alkaline phosphatase (EC 3.1.3.1).

The detection system I described above is replaced by the following:

Detection system II (with carboxypeptidase A)

0.2 ml D-luciferyl-(L)-phenylalanine solution
(10 µmole/l in 0.05 mole/l Tris/HCl, 3 g/l LiCl pH 7.5)
Incubated for 1 h at 37° C.

Detection system III (with carboxypeptidase B)

0.2 ml D-luciferyl-(L)-N-α-arginine solution
(10 µmole/l in 0.05 mole/l Tris/HCl, 0.2 mole/l NaCl, pH 7.8)
Incubated at 37° C. for 1 h.

Detection system IV (with arylsulfatase)

0.2 ml D-luciferin-O-sulfate solution
(10 µmole/l in 10 mmole/l sodium acetate, pH 5.0)
Incubated at 37° C. for 1 h.

Detection system V (with alkaline phosphatase)

0.2 ml D-luciferin-O-phosphate solution
(10 µmole/l in 10 mmole/l diethanolamine, 0.5 mmole/l in $MgCl_2a$ $6H_2O$ pH 9.8)
Incubated at 37° C. for 1 h.

In the above example the determination of bradykinin is explained. In place of these analytes, other analytes may also be determined, for example insulin, tyroxin $T_3$ and tyroxin $T_4$.

EXAMPLE B

Immuno Assay for the Determination of Proteins, for Example Human Kallikrein 0.2 ml of a human urine kallikrein solution (10 µg/ml in buffer A) are introduced into the depressions of a microtiter plate and incubated overnight at 4° C. This antigen adheres due to hydrophobic interactions to the surface of the microtiter plate. Subsequently, the plate is washed five times with the buffer B (automatically in the washer).

Parallel to this preparation, 0.5 ml of an anti-human kallikrein immunoglobulin solution (10 ng) with 0.5 ml of a human kallikrein solution (in different concentrations) is incubated overnight at 4° C.

Subsequently, 0.2 ml each of the latter incubation preparation are introduced into the coated depressions of the microtiter plates and incubated 3 h at 37° C. In the process, the antibodies not yet occupied by human kallikrein antibodies are bonded to the human kallikrein adhering to the microtiter plate.

0.2 ml of an anti-rabbit immunoglobulin alkaline phosphatase conjugate solution (1 μconjugate/ml buffer C; from a goat) is introduced into the depressions and incubated for 3 h at 37° C. In the process, the conjugate is bonded to the antigen-antibody combination. But the conjugate can attach itself only if the aforementioned antibody is present. The greater the quantity of antibodies, the higher will be the amount of the bound conjugate. The method represents an indirect enzyme immuno assay for human urine kallikrein.

According to the method, 0.2 ml of a luciferin-O-phosphate solution ($1 \times 10^{-5}$ mole/l in 10 mmole/l diethanolamine, 0.5 mmole/l $MgCl_2$. 6 $H_2O$, pH 9.8) is introduced into the depressions of the microtiter plate and incubated for 1 h at 37° C. After the incubation, 0.1 ml is taken from each of the depressions and pipetted into the "bioluminescence cocktail" described in Example A. Light pulses are then measured for 10 sec (Detection system V).

The more of the conjugate is bound to the solid carrier, the more luciferin is released and the higher will be the luminous yield.

Figure 2:
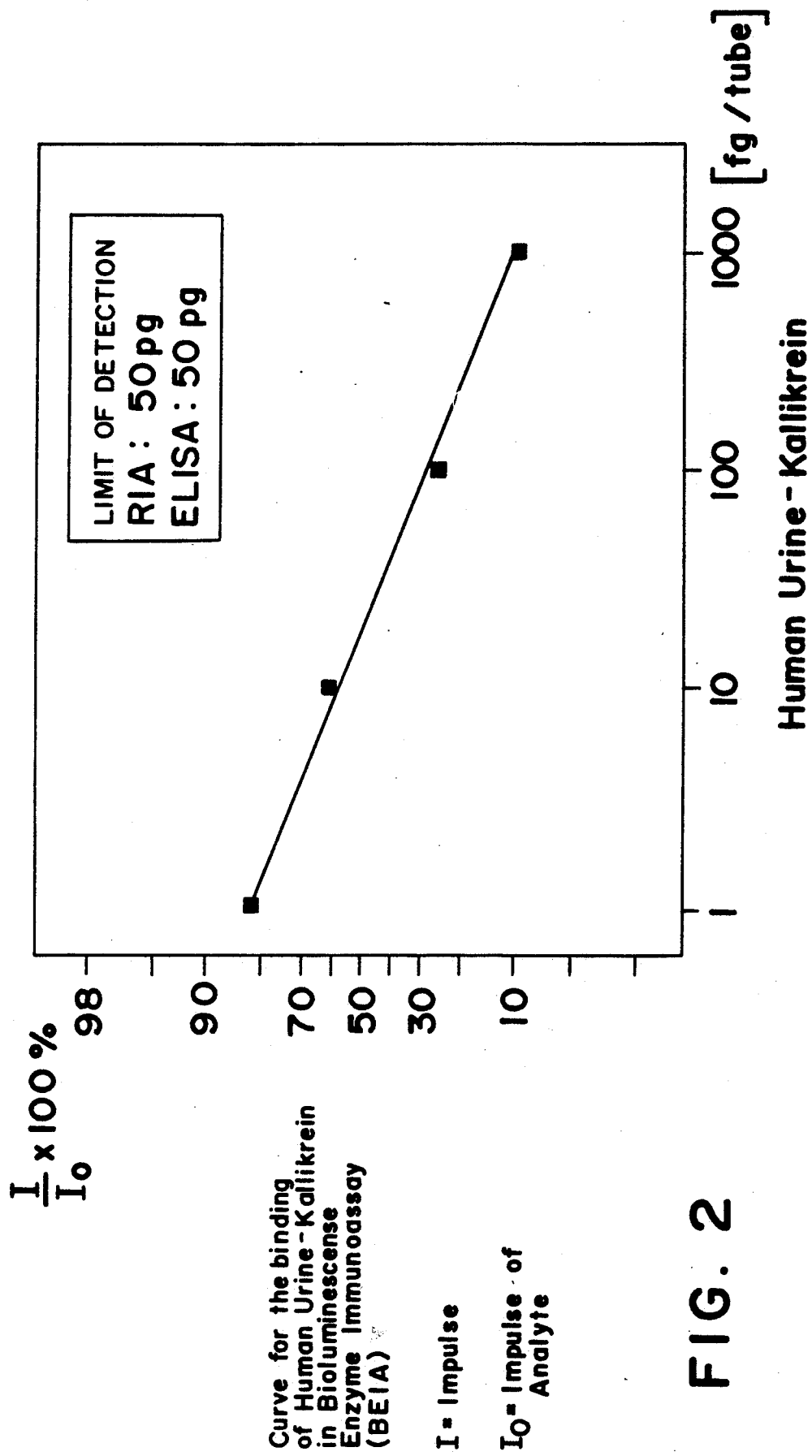

A standard curve may be established from the data obtained; it is shown in FIG. 2. As may be seen, the concentration of human kallikrein may be determined within a range of $10^{-15}$ to $10^{-12}$ [g/cavity].

The limit of detection obtained with the enzyme immuno assays heretofore was $5 \times 10^{-9}$ [g/cavity], see: J. Clin. Chem. Clin. Biochem. Vol. 18, 1980, pages 197-208).

In the above example, the enzyme used, i.e. the alkaline phosphatase, may be replaced by carboxylesterase, carboxypeptidase A and B and arylsulfatase. In this case detection systems I, II, III or IV are used.

By means of the immuno assay described in this example not only human urine kallikrein, but also granulocytenelastase of swine, $\alpha_1$-proteinase inhibitor of swine, plasmakallikrein, cytochrome, immunoglobulin G, M, E and A, fibrinogen and fibrinogen fission products (fibrinopeptides A, B and C) may be determined.

EXAMPLE C

Determination of Antibodies Specific for Human Urine Kallikrein 0.2 ml of a human urine kallikrein solution (10 μg/ml in buffer A) is introduced into the depressions of a microtiter plate and incubated at 4° C. This antigen adheres due to hydrophobic interactions to the surface of the microtiter plate. The plate is subsequently washed five times with buffer B (automatically in washer).

The antibody-containing serum (obtained for example from rabbits) is then added in different concentrations into the corresponding depressions of the microtiter plate and incubated 3 h at 37° C. (the antiserum is diluted with buffer C). In the process the antibody bonds to the antigen as a function of concentration. Subsequently, the plate is again washed five times with buffer B.

After this, 0.2 ml of an antirabbit immunoglobin-esterase conjugate solution (50 μl conjugate/ml buffer C; obtained from a goat) is introduced in the depressions and incubated 3 h at 37° C. In the process, the conjugate bonds to the antigen-antibody combination. The conjugate can bond only if the aforementioned antibody is present. The higher the amount of the antibody, the higher the quantity of the bound conjugate will be. Subsequently, 0.2 ml of a luciferin methyl ester solution ($2 \times 10^{-6}$ mole/l in 50 mmole/l Tris/HCl; pH 7.5) is added to the depression of the microtiter plate and incubated 1 h at 37° C. After the incubation, 0.1 ml each is taken from the depressions and pipetted into the "bioluminescent cocktail" described in Example A. Light pulses are measured for 10 sec.

The more of the conjugate is bonded to the solid carrier, the more luciferin is released and the higher will be the luminous yield.

Based on the data obtained, a standard curve may be established; it is shown in FIG. 3. It may be seen that the concentration of the antibody for human urine kallikrein (anti-HUK-IgG) may be determined within a range of $10^{-12}$ to $10^{-9}$ [g/cavity].

The limit of detection obtained with the enzyme immuno assays known heretofore was around $5 \times 10^{-9}$ [g/cavity]. See: J. Clin. Chem. Clin. Biochem. Vol. 18, 1980, pages 197-208.

With this assay antibodies may be determined against the following analytes:

bradykinin, human urine kallikrein, granulocyte elastase of swine, α-proteinase inhibitor of swine, plasmakallikrein, cytochrome, immunoglobulin G, M, E and A, insulin, tyroxin $T_3$ and $T_4$, fibrinogen and fibrinogen fission products (fibrinopeptides A, B and C).

EXAMPLE D

Sandwich Enzyme Immunoassay for Human Urine Kallikrein

Into the depressions of microtiter plate (Dynatech Co.) immune selected anti-HUK-IgG of goat (10 μg/ml in Buffer A; 0.2 ml/cavity) are introduced and incubated overnight at 4° C. Subsequently, the plate is washed five times with buffer B and 0.2 ml of a solution of human urine kallikrein (in buffer C) pipetted into the depressions and incubated 24 h at 4° C. Following a repeated washing with buffer B, it is incubated for 24 h with anti-HUK-IgG of rabbit (10 μg/ml buffer C). The plate is then washed five times with buffer B and incubation continued for another 24 h with anti-rabbit-IgG-enzyme conjugate (0.2 ml buffer C), with carboxylesterase, carboxypeptidase A and B, arylsulfatase or alkaline phosphatase, being used as the enzyme. Depending on the enzyme, detection systems I to V are used to determine the bound anti-rabbit-IgG-enzyme conjugate.

Examples of further applications of the detection system according to the invention.

EXAMPLE E

Carrying Out a Blot Process (Western Blot—Actual Example: Protein Inhibitor Against Leukocyte Elastase of Swine)

As described in the literature (1), initially a SDS electrophoresis is carried out with the inhibitor. After this, the protein is transferred from the acrylamide gel to a nitrocellulose sheet (1). Subsequently, the "blotted" (transferred) inhibitor is rendered visible as follows:

The nitrocellulose sheet is incubated for 24 h at room temperature with antibody-alkaline phosphatase conjugate in buffer B (the antibody is directed agains the inhibitor). The sheet is then washed with buffer A and the nitrocellulose sheet placed in a trough wetted with the bioluminescence cocktail and 10 μmole/l D-lucifer-in-O-phosphate. (The viscosity of the bioluminescence cocktail has been increased by means of gelling agent (for example agar). This entirety is placed with the exclusion of light onto a highly sensitive S/W film (Kodak TRI-X pan professional film) and exposed for 2 h to radiation at room temperature. The position of the inhibitor may be determined by the black coloration.

Literature for the blot method:

1) Twobin et al. (1979), Proc. Natl. Acad. Sci. USA 76, 4350.

Literature for nucleic acid hybridization:

Southern E. M. (1980) Meth. Enzymol. 68, 152.

Alwine et al (1980) Meth. Enzymol. 68, 220.

Buffer A: 10 mmole/l $KH_2PO_4$, 15 mmole/l NaCl, 0.05 g/l Tween 20 pH 7.4

Buffer B: 1.5 mmole/l $KH_2PO_4$. $H_2O$, 0.14 mole/l NaCl, 0.5 g/l Tween, 20.2 mg/ml cattle serum albumin, pH 7.4.

EXAMPLE F

Carrying Out a Nucleic Acid Hybridization Process (Southern Blot—Actual Example: pBR322 Hybridization):

pBR322 DNA is, as described in the literature (2), isolated from E. coli and separated in acrylamide gel electrophoretically. Subsequently, the hybridization is carried out on nitrocellulose as follows:

The nitrocellulose is treated as described in references 2 and 3. Then, not as usual a radioactively marked pBr322 DNA is used for hybridization, but a pBr322 DNA marked with biotin by means of a Nick translation (Bethesda Research Laboratories Kit or Ref. 2; describe the marking of DNA with biotin). The nitrocellulose sheet is incubated for 2 h at 37° C. with a streptavidine phosphatase conjugate in buffer A (the streptavidine bonds specifically to the biotinylated pBr322 DAN). The sheet is then washed with buffer A and the nitrocellulose sheet placed into a trough wetted with the bioluminescence cocktail and 10 μmole/l D-luciferin-O-phosphate (the bioluminescence cocktail was made more viscous with gelling agents, for example agar). The entire preparation is placed onto a high sensitivity S/W film (Kodak TRI-X pan professional film) and exposed for 2 h to radiation at room temperature. The film is then developed and the position of the inhibitor may be determined by black coloration.

(2) Maniatis et al. (1982) Molecular Cloning, Cold Spring Harber Laboratory (3) B. D. Hames and S. J. Higgins (1985), Nucleic Acid Hybridization, a Practical Approach, IRL Press, Oxford Buffer A: 10 mmole/l $KH_2PO_4$, 15 mmole/l NaCl, 0.05 g/l, Tween 20 pH 7.4

Buffer B: 1.5 mmole/l $KH_2PO_4$. $H_2O$, 0.14 mole/l NaCl, 0.5 g/l Tween 20, 2 mg/ml cattle serum albumin, pH 7.4

EXAMPLES OF PREPARATION

EXAMPLE 1

Preparation of D-luciferon-hydroxysuccinic-imide-ester (L-O-Su: intermediate compound)

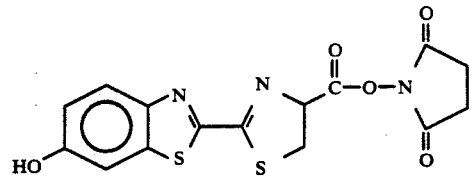

30 mg (0.11 mmole) D-luciferin* and 12.4 mg (0.11 mmole) N-hydroxysuccinic-imide are dissolved at room temperature in 1.8 ml tetrahydrofuran (THF). To this solution 24.7 mg (0.12 mmole) N,N-dicyclohexylcarbodiimide (dissolved in 0.1 ml THF) are added and the solution allowed to stand for 3 h with the exclusion of light. The urea precipitated is filtered off, the clear solution obtained added with shaking to 21 ml n-hexane, the flocculated precipitate is suctioned off and dried in a desiccator. Yield: 33 mg (80% of theoretical).

| *D-luciferin: D-(-)-2-(6'-hydroxy-2'-benzothiazolyl)-$\Delta^2$-thiazoline-4-carboxylic acid Analysis for $C_{15}H_{11}N_3S_2O_5$ MW: 377.40 | | | |
|---|---|---|---|
| | C | H | N |
| calculated: | 49.68 | 3.66 | 10.53 |
| determined: | 49.39 | 3.77 | 10.54 |

EXAMPLE 2

Purification of D-luciferin methyl ester

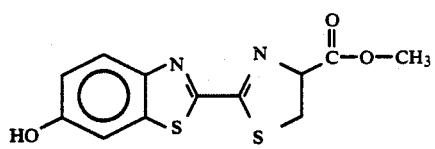

D-luciferin methyl ester is prepared according to E. H. White, J. Amer. Chem. Soc. 102, 3199 (1980).

Purification is effected by column chromatography on silica gel (Kieselgel 60, Merck 9385), with benzol-ethylacetate as the elutant. Yield: 69% of theoretical.

| Analysis for $C_{12}H_{10}N_2S_2O_3$ MW: 294.35 | | | |
|---|---|---|---|
| | C | H | N |
| calculated: | 48.97 | 3.42 | 9.52 |
| determined: | 49.59 | 3.77 | 9.41 |

The mass spectrum and the UV spectrum are in agreement with the structure.

EXAMPLE 3

Preparation of D-luciferyl-L-N-α-arginine

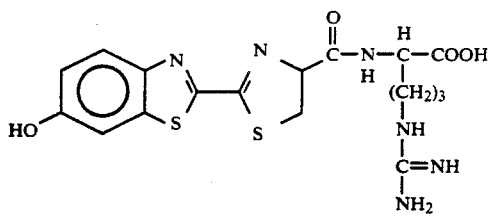

C₁₇H₂₀N₆S₂O₄; MW: 436.52

12.25 mg (30 μmole) L-O-Su (prepared according to Example 1) is dissolved in 0.3 ml dioxane and diluted with 0.2 ml of a 0.6 mole/l (120 μmole) L-arginine solution with pH 7.5 (prepared by dissolving arginine in water and adding 2N HCl to pH 7.5). After 10 min, 0.015 ml 2N NaOH is added and the pH of the solution adjusted to 6. The reaction mixture is left to stand for 2 h at room temperature. Dioxane is evaporated in a rotating evaporator, taken up in water, 1 mole/l ammonia added until everything is dissolved, the solution filtered and purified with HPLC (column: Hibar EC-RP 8 Merck; Sol.-A: 0.05 mole/l ammonium acetate pH 6.5; Sol.-B: methanol for chromatography; A:B=65:35; flow 1 ml/min; pressure approx. 170 bar). The yield is 4.81 mg (37% of theoretical). UV maximum: 265, 335 mm (phosphate buffer pH 7.5). Fluorescent spectrum: excitation 333 nm; emission 544 nm (phosphate buffer pH 7.8)

Amino acid analysis: 0.96 mole arginine per mole D-(−)-luciferin.

EXAMPLE 4

Preparation of D-luciferyl-L-phenylalanine

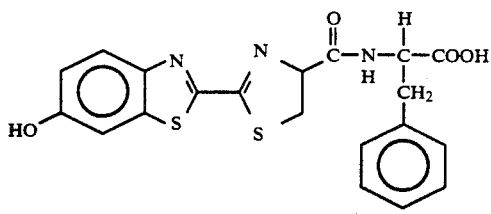

4.4 mg (26.5 μmole) L-phenylalanine are dissolved in 0.2 ml dioxane and 0.1 ml water with the addition of 0.06 ml triethylamine. This solution is added to 10 mg (26.5 μmole) L-O-Su (prepared according to Example 1) and let stand for 2 h at room temperature. Subsequently, 0.01 ml acetic acid and 1 ml water are added and stored overnight at 4° C. The precipitate is centrifuged off, dissolved in 0.1 mole/l ammonia and purified with HPLC. The yield is 6.52 mg (63% of theoretical).

Overall formula: C₂₀H₁₇N₃O₄S₂; MW: 402.49.

UV maximum: 270, 335 nm (phosphate buffer 7.5).

Fluorescent spectra: excitation 332 nm; emission 543 nm (phosphate buffer 7.5).

Amino acid analysis: 1.02 mole phenylalanine per mole D-(−)-luciferin.

EXAMPLE 5

Preparation of D-luciferyl-L-methione

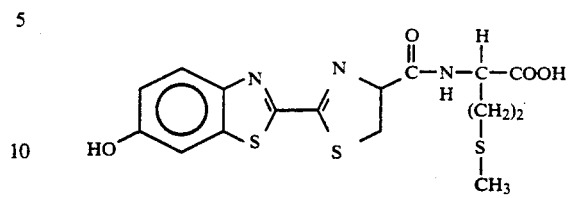

Overall formula: C₁₆H₁₇N₃O₄S₃; MW 411.52.

The operation is carried out as in Example 4, but phenylalanine is replaced by an equimolar amount of L-methione, whereby the abovecaptioned compound is obtained.

UV maximum: 265, 335 nm (phosphate buffer 7.5)

Fluorescent spectrum: excitation 340 nm; emission 43: nm (methanol)

Amino acid analysis: 0.98 mole methionine per mole of D-(−)-luciferin

EXAMPLE 6

Preparation of D-luciferyl-L-glycine

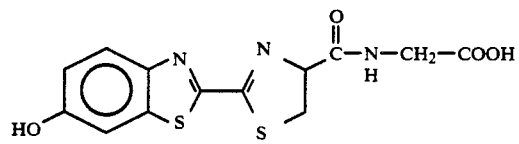

Overall formula: C₁₃H₁₁N₃O₄S₂; MW337.37.

The operation is carried out as in Example 4, but the phenylalanine is replaced by an equimolar amount of L-glycine, whereby the above captioned compound is obtained.

UV maximum: 265, 335 nm (phosphate buffer 7.5).

Fluorescent spectrum: excitation 348 nm; emission 435 nm (methanol).

Amino acid analysis: 0.94 mole glycine per mole of D-(−)-luciferin.

EXAMPLE 7

Preparation of D-luciferin-)-sulfate

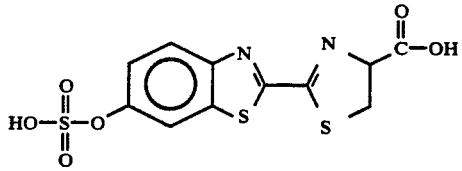

20 mg (71 μmole) D-luciferin are dissolved in 0.6 ml dry pyridine. The solution is added to 16 mg (100 μmole) of a pyridine-SO₃ complex. The solution is allowed to stand for 2 h at room temperature and purified with HPLC as in Example 3. The yield is 37% of theoretical.

UV maximum: 250, 290 nm (phosphate buffer 7.5).

Fluorescent spectrum: excitation 338 nm; emission 412 nm (phosphate buffer pH 5.0).

Overall formula: C₁₁H₈N₂O₆S₃; MG: 360.39.

EXAMPLE 8

Preparation of D-luciferin-O-phosphate

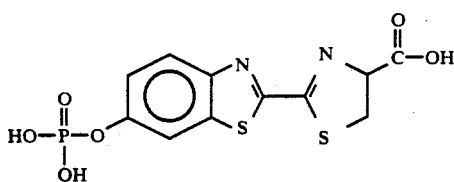

50 mg (180 μmole) D-luciferin is dissolved in 2 ml water and mixed with 350 mg (8.75 mmole) magnesium oxide. To the cooled suspension, slowly and drop by drop a solution of 92 mg (600 μmole) phosphoroxychloride in 1 ml carbon tetrachloride is added. It is then allowed to stand for 30 min at room temperature, filtered and neutralized with acetic acid. After concentration, it is purified with HPLC as in Example 3. The yield is 29% of theoretical.

UV maximum: 260, 315 nm (phosphate buffer pH 7.5).

Fluorescent spectrum: excitation 345 nm; emission 442 nm.

Overall formula: $C_{11}H_9N_2O_6S_2P_1$; MW: 359.39.

EXAMPLE 9

Preparation of D-luciferin amide

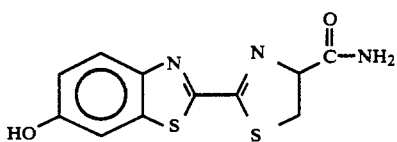

12.25 mg (30 μmole) L-O-Su (prepared as in Example 1) are dissolved in 0.3 ml dioxane and diluted with 0.2 ml of a 0.6 mole/l (129 μmole) ammonia solution. The reaction mixture is allowed to stand for 2 h under nitrogen at room temperature. The solution is concentrated in a rotating evaporator to dryness. The residue is taken up in a little dilute ammonia, filtered and purified with HPLC (column: Hibar EC-RP 8 Merck; sol. A: 0.05 mol/l ammonia acetate pH 6.6; sl. B: methanol for chromatography; A:B=65:35; flow 1 ml/h; pressure: approx. 170 bar). The yield is 7.4 mg (82% of theoretical).

Overall formula: $C_{12}H_9N_3S_2O_2$; MW: 279.34.

EXAMPLE 10

Preparation of D-luciferin-n-hexane ester

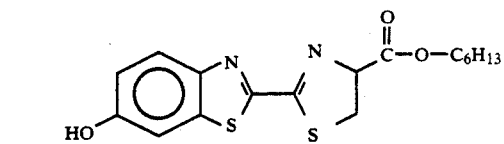

40 mg (0.14 mmole) D-luciferin are dissolved under nitrogen in absolute tetrahydrofurane and cooled to −15° C. Subsequently, the solution is mixed with 23 μl (0.16 mmole) triethylamine and 21 μl (0.16 mmole) chloroformic acid butylester and agitated for 30 min at −15° C. 38 μl (0.03 mmole) n-hexanol are added drop by drop, the solution heated slowly to room temperature and agitated overnight at this temperature. Subsequently the triethylamine-hydrochloride is filtered out, the filtrate concentrated and taken up in a little methanol. Purification is effected with HPLC as in Example 3. The yield is 6.6 mg (34% of theoretical).

Overall formula: $C_{17}H_{20}N_2S_2O_3$; MW: 364.49.

EXAMPLE 11

Preparation of D-luciferin-trans-hex-3-ene ester

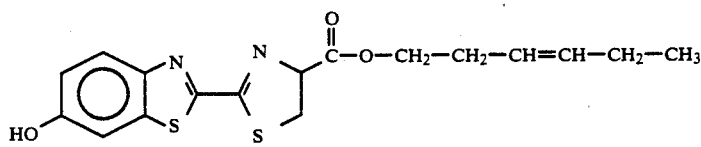

40 mg (0.14 mmole) D-luciferin are dissolved under nitrogen in absolute tetrahydrofurane and cooled to −15° C. Subsequently, the solution is mixed with 23 μl (0.16 mmole) triethylamine and 21 μl (0.16 mmole) chloroformic acid isobutylester and agitated for 30 min at −15° C. 37 μl (0.3 mmole) trans-3-hexen-1-ol are added drop by drop, allowed to warm slowly to room temperature and agitated overnight at this temperature. The triethylamine hydrochloride precipitated is filtered out, the filtrate concentrated and taken up in a little methanol and purified with HPLC as in Example 3. The yield is 5.6 mg (29% of theoretical).

Overall formula: $C_{17}H_{18}N_2S_2O_3$; MW: 362.47.

EXAMPLE 12

Preparation of D-luciferyl-L-histidyl-L-leucine

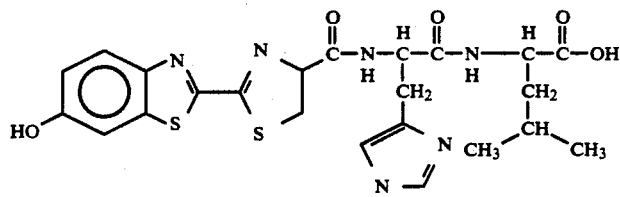

7.1 mg (26.5 μmole) L-histidyl-L-leucine are dissolved in 0.2 ml dioxane and 0.1 ml water with the addition of 0.06 ml triethylamine. This solution is added to 10 mg (26.5 μmole) L-O-Su in 0.5 ml dioxane (prepared as in Example 1) and allowed to stand for 2 h at room temperature. It is then neutralized with acetic acid, 1 ml water added and stored overnight at 4° C. The precipitate is centrifuged off, dissolved in 0.1 mole/l ammonia and purified with HPLC. The yield is 5.3 mg (39% of theoretical).

Overall formula: $C_{23}H_{27}N_6S_2O_5$; MW: 513.63.

EXAMPLE 13

Preparation of D-luciferyl-arginyl-prolyl-prolyl-glycyl-phenylalanylserin

[Structure: benzothiazole-thiazoline-C(=O)-N(H)-ArG-PRO-PRO-GLY-PHE-SER]

17.5 mg (26.5 μmole) L-arginyl-prolyl-glycyl-phenylalanylserin are dissolved in 0.2 ml dioxane and 0.1 ml water, with the addition of 0.06 ml triethylamine. This solution is added to 10 mg (26.5 μmole) L-O-Su in 0.5 ml dioxane (prepared as in Example 1) and allowed to stand for 2 h at room temperature. Subsequently it is neutralized with acetic acid, 1 ml water added and stored overnight at 4° C. The precipitate is centrifuged off, dissolved in 0.1 mole/l ammonia and purified with HPLC. The yield is 10.3 mg (42% of theoretical).

Overall formula: $C_{41}H_{52}N_{11}S_2O_{10}$; MW 923.08.

EXAMPLE 14

Preparation of D-luciferyl-L-ornithine

[Structure of D-luciferyl-L-ornithine]

13.2 mg (0.053 mmole) N-BOC-L-ornithine are dissolved in 0.6 ml dioxane with the addition of 0.12 ml triethylamine. This solution is added to 20 mg (53 μmole) L-O-Su in 0.5 ml dioxane (prepared as in Example 1) and allowed to stand for 2 h at room temperature. It is then neutralized with acetic acid, 2 ml water added and stored overnight at 4° C. The precipitate is centrifuged off and dried over phosphorpentoxide. It is then suspended in 1 ml trifluoroacetic acid and agitated with the exclusion of water and under nitrogen for 1 h at room temperature. The suspension is concentrated, taken up in a little dilute ammonia and purified with HPLC. The yield is 8.8 mg (42% of theoretical).

Overall formula: $C_{16}H_{18}N_6S_2O_4$; MW: 394.19.

EXAMPLE 15

Preparation of D-luciferyl-L-homoarginine

[Structure of D-luciferyl-L-homoarginine]

12.25 mg (0.030 mmole) L-O-Su (prepared as in Example 1) in 0.3 ml dioxane and mixed with 0.2 ml of a 0.6 mole/l (120 μmole) L-homoarginine solution with pH 7.5 (prepared by dissolving homoarginine in water and with the addition of 2N HCl to pH 7.5). After 10 min. the pH of the solution is adjusted to 6. The reaction mixture is allowed to stand for 2 h at room temperature. It is then concentrated in a rotating evaporator, taken up in a little dilute ammonia, filtered and purified with HPLC. The yield is 4.5 mg (33% of theoretical).

Overall formula: $C_{16}H_{18}N_6S_2O_4$; MW: 422.35.

EXAMPLE 16

Preparation of D-luciferyl-L-citrulline

[Structure of D-luciferyl-L-citrulline]

12.25 mg (0.030 mmole) L-O-Su (prepared as in Example 1) is dissolved in 0.3 ml dioxane and mixed with 21 mg (0.12 mmole) L-citrulline in 0.2 ml water. After 10 min, the pH of the solution is adjusted to 6. The reaction mixture is allowed to stand for 2 h at room temperature. It is then concentrated in a rotating evaporator, taken up in a little dilute ammonia, filtered and purified with HPLC. The yield is 6.3 mg (43% of theoretical).

Overall formula: $C_{17}H_{20}N_5S_2O_5$; MW: 453.21.

EXAMPLE 17

Preparation of D-luciferyl-L-aminobutyric acid

[Structure of D-luciferyl-L-aminobutyric acid]

5.1 mg (26.5 μmole) diaminobutyric acid×2 HCl are dissolved in 0.2 ml dioxane and 0.1 water with the addition of 0.06 ml triethylamine. This solution is added to 10 mg (26.5 μmole) L-O-Su (prepared as in Example 1) in 0.5 ml dioxane and allowed to stand for 2 h at room temperature. Subsequently, 0.01 ml acetic acid and 1 ml water are added and the mixture stored overnight at 4° C. The precipitate is centrifuged off, dissolved in 0.1 mole/l ammonia and purified with HPLC. The yield is 5.3 mg (39% of theoretical).

Overall formula: $C_{15}H_{16}N_4S_2O_4$; MW: 469.69.

EXAMPLE 18

Preparation of D-luciferin-O-hexanoic acid ester

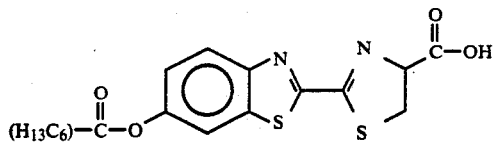

30 mg (0.1 mmole) D-luciferinmethylester are dissolved in 2 ml dry pyridine. To the cooled solution, slowly, drop by drop, a solution of 0.028 ml (0.2 mmole) hexanoic acid in 1 ml dry carbon tetrachloride is added. It is then allowed to warm to room temperature, filtered and concentrated in vacuum. The methyl group is then split off by means of carboxylesterase (the residue is dissolved in 0.05 mole/l tris/HCl, pH 8.5, centrifuged off the insoluble material, mixed with 5 U carboxylesterase and incubated for 2 h under nitrogen at 37° C. It is then purified with HPLC as in Example 3. The yield is 12.3 mg (32% of theoretical).

Overall formula: $C_{17}H_{18}N_2S_2O_4$; MW: 378.48.

EXAMPLE 19

Preparation of D-luciferin-O-trans-3-hexanoic acid ester

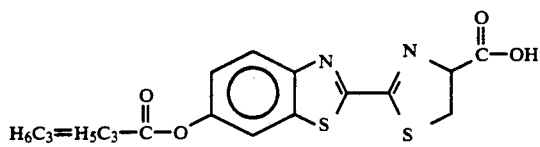

30 mg (0.1 mmole) D-luciferinmethylester are dissolved in dry pyridine. To the cooled solution, drop by drop a solution of 0.022 ml (0.2 mmole) trans-3-hexenoic acid chloride in 1 ml dry carbon tetrachloride is added. The solution is allowed to warm to room temperature, filtered and concentrated in vacuum. The methyl group is split off with carboxylesterase (the residue is dissolved in tris/HCl, pH 8.5, centrifuged off the insoluble material, mixed with 5 U carboxylesterase and incubated for 2 h under nitrogen at 37° C.). It is then purified with HPLC as in Example 3. The yield is 7.3 mg (19% of theoretical).

Overall formula: $C_{17}H_{16}H_2S_2O_4$; MW: 376.45.

EXAMPLE 20

Preparation of D-luciferin-O-palmityl ester

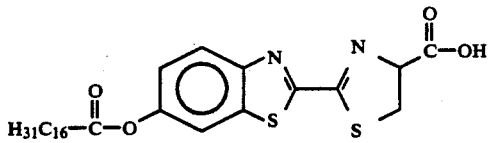

30 mg (0.1 mmole) D-luciferinmethylester are dissolved in 2 ml dry pyridine. To the cooled solution, drop by drop a solution of 99 mg (0.2 mmole) hexadecanoic acid chloride in 1 ml dry carbon tetrachloride is added. The solution is then allowed to warm to room temperature, filtered and concentrated in vacuum. The methyl group is then split off with carboxylesterase (the residue is dissolved in 0.05 mole/l tris/HCl, pH 8.5, centrifuged off the insoluble material, mixed with 5 U carboxylesterase and incubated for 2 h under nitrogen at 37° C.). Subsequently, it is purified with HPLC as in Example 3. The yield is 7.9 mg (15% of theoretical).

Overall formula: $C_{27}H_{38}N_2S_2O_4$; MW: 518.75.

EXAMPLE 21

Preparation of D-luciferin-O-benzoic acid ester

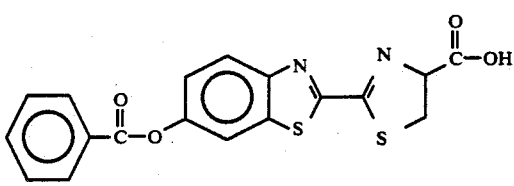

30 mg (0.1 mmole) D-luciferinmethylester is dissolved in 2 ml dry pyridine. To the cooled solution drop by drop a solution of 28 mg (0.2 mmole) benzoic acid chloride in 1 ml dry carbon tetrachloride is added. The solution is then allowed to warm to room temperature, filtered and concentrated in vacuum. The methyl group is then split off with carboxylesterase (the residue is dissolved in 0.05 mole/l tris/HCl, pH 8.5, centrifuged off the insoluble material, mixed with 5 U carboxylesterase and incubated for 2 h under nitrogen at 37° C.). Subsequently, it is purified with HPLC as in Example 3. The yield is 9.8 mg (25% of theoretical).

Overall formula: $C_{18}H_{12}N_2S_2O_4$; MW: 384.44.

EXAMPLE 22

Preparation of D-luciferin-O-naphthanic acid ester

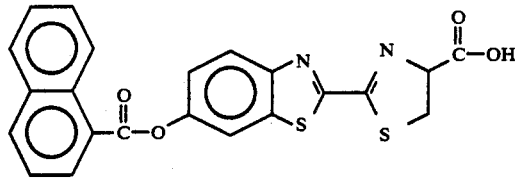

30 mg (0.1 mmole) D-luciferinmethylester are dissolved in 2 ml dry pyridine. To the cooled solution, slowly, drop by drop, a solution of 38 mg (0.2 mmole) 1-naphthyl chloride in 1 ml dry carbon tetrachloride is added. The solution is then allowed to warm to room temperature, filtered and concentrated in vacuum. The methyl group is split off with carboxylesterase (the residue is dissolved in 0.05 mole/l tris/HCl, pH 8.5, centrifuged off the insoluble material, mixed with 5 U carboxylesterase and incubated for 2 h under nitrogen at 37° C.). It is then purified with HPLC as in Example 3. The yield is 5.3 mg (12% of theoretical).

Overall formula: $C_{22}H_{14}N_2S_2O_4$; MW: 434.50.

EXAMPLE 23

Preparation of D-luciferin-o-(C1)glucose

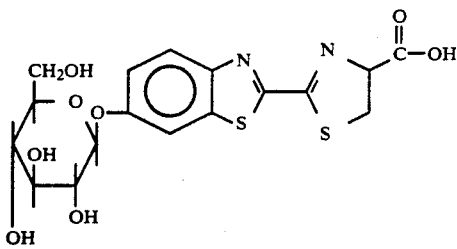

D-glucose was acetylated as described in the literature (1) with acetanhydride to D-glucosepyranose-pentaacetate. Subsequently, tetraacetyl-a-D-glucopyranosyl bromide is prepared by the action of HBr.

60 mg (0.2 mmole) D-luciferinmethylester are dissolved in 10 ml water and mixed with 280 mg (7 mmole) magnesium oxide. To the cooled suspension slowly 162 mg (0.4 mmole) tetraacetyl-a-D-glucopyranosyl bromide are added. It is then allowed to stand for 48 h at 40° C., filtered and neutralized with dilute ammonia. After concentration the methyl radical is split off with carboxylesterase (the residue is dissolved in 0.05 mole/l tris/HCl, pH 7.5, centrifuged off the insoluble material, mixed with 5 U carboxylesterase and incubated for 2 h at 25° C.). The acetyl residues of tetraacetyl-a-D-glucopyranose are split off by ammonolysis. Purification is effected with HPLC as in Example 3. The yield is 7.2 mg (8% of theoretical).

Overall formula: $C_{17}H_{13}N_2S_2O_9$; MW: 441.46.

(1) Acetylation of Sugars, Houben-Weyl-Muller, Methods of Organic Chemistry.

EXAMPLE 24

Preparation of D-luciferin-O-(C1)galactose

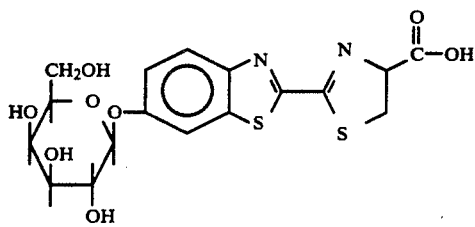

D-galactose is acetylated as described in the literature (1) with acetanhydride to D-galactopyranose-pentaacetate. Subsequently, tetraacetyl-a-D-galactopyranosyl bromide is prepared by the action of HBr.

60 mg (0.2 mmole) D-luciferinmethylester are dissolved in 10 ml water and mixed with 280 mg (7 mmole) magnesium oxide. To the cooled suspension, slowly 162 mg (0.4 mmole) tetraacetyl-a-D-galactopyranosyl bromide. It is then allowed to stand for 48 h at 40° C., filtrated and neutralized with dilute ammonia. After concentration, the methyl radical is split off with carboxyesterase (the precipitate is dissolved in 0.05 mole/l tris/HCl, pH 75, centrifuged off the insoluble material, mixed with 5 U carboxylesterase and incubated for 2 h at 25° C.). The acetyl radicals of tetra-acetyl-a-D-galactopyranose are split off by ammonolysis. Purification is effected with HPLC as in Example 3. The yield is 5.4 mg (6% of thereotical).

Overall formula: $C_{17}H_{13}N_2S_2O_9$; MW: 441.46.

EXAMPLES 25 AND 26

Preparation of D-luciferin-O-(C1)manose and D-luciferin-O-(C1)ribose

These compounds may be prepared analogously to the synthesis of D-luciferin-O-(C[1])glucose (described in Example 21).

EXAMPLE 27

Preparation of D-luciferin-O-(C[1])maltose

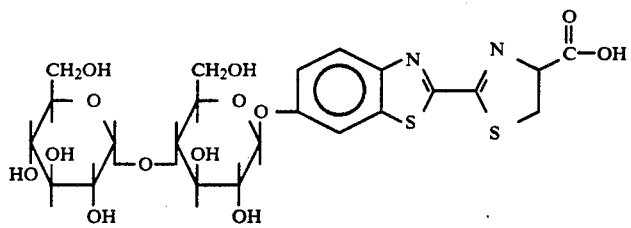

Maltose is acetylated, as described in the literature (1), with acetanhydride to maltose-octaacetate. Subsequently, heptaacetyl-manose bromide is prepared by the action of HBr.

60 mg (0.2 mmole) D-luciferinmethylester are dissolved in 10 ml water and mixed with 280 mg (7 mmole) magnesium oxide. To the cooled suspension, slowly 243 mg (0.4 mmole) heptaacetyl-manose bromide are added. The suspension is allowed to stand for 48 h at 40° C., filtered and neutralized with dilute ammonia. After concentration, the methyl radical is split off with carboxylesterase (the residue is dissolved in 0.05 mole/l tris/HCl, pH 7.5, centrifuged off the insoluble material, mixed with 5 U carboxylesterase and incubated for 2 h at 25° C.). The acetyl radicals of the heptaacetyl-manose are split off by ammonolysis. Purification is with HPLC as described in Example 3. The yield is 6.1 mg (5% of theoretical).

Overall formula: $C_{23}H_{27}N_2S_2O_{13}$; MW: 600.45.

EXAMPLE 28

Preparation of D-luciferin-O-dAMP

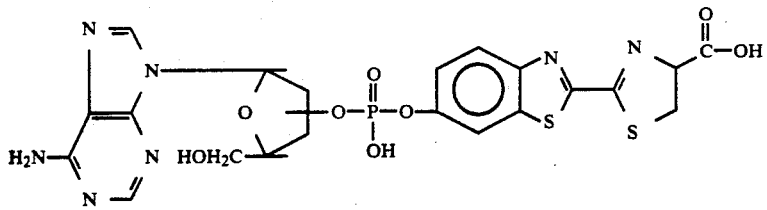

60 mg (0.2 mmole) D-luciferinmethylester are dissolved in 10 ml anhydrous pyridine and mixed with 166 mg (0.2 mmole) $N^6$-benzoyl-5'-O-(4,4'-dimethoxytrityl)-2'-deoxyadenosine-3'-(2-chlorophenyl)-phosphate. The entire mixture is again taken up in 20 ml dry pyridine, mixed with 170 mg (0.6 mmole) mesitylene-sulfonyltetrazole and incubated for 4 h at room temperature. The reaction mixture is then mixed with 10 ml water and rotated to dryness. The residue is dissolved in ice cold acetone, washed with a 5% $NaHCO_3$ solution and water. The organic phase is dried over sodium sulfate and concentrated by rotation. The protective groups are split off as described in the literature (2) and the substance purified with HPLC. The yield is 14 mg (12% of theoretical).

Overall formula: $C_{20}H_{18}N_7S_2O_8P$; MW: 580.80.

(2) Meth. Enzymol. 65, 610 (1980).

EXAMPLES 29 TO 31

Preparation of D-luciferin-O-dGMP, D-luciferin-O-dCMP and D-luciferin-O-TMP

These compounds may be prepared analogously to Example 28, wherein, however, $N_6$-benzoyl-5'-O-(4,4'-dimethoxytrityl)-2'-deoxyadenosine-3'-(2-chlorophenyl)-phosphate is replaced by $N^2$-isobutyryl-5'-O-(4,4'-dimethoxytrityl)-2'-deoxyguanosine-3'-(2-chlorophenyl)-phosphate, $N^4$-benzoyl-5'-O-(4,4'-dimethoxytrityl)-2'-deoxycytidine-3'-(2-chlorophenyl)-phosphate or 5'-O-(4,4'-dimethoxytrityl)-2'-thymidine 3'-(2-chlorophenyl)-phosphate, respectively.

From the compound described in Examples 9 to 31 D-luciferin may be released by means of the enzymes listed in the following table.

TABLE

| Example No. | Enzyme used |
|---|---|
| 9 | Amidase (EC 3.5.1.4) |
| 10 | Carboxylesterase (EC 3.1.1.1) |
| 11 | Carboxylesterase (EC 3.1.1.1) |
| 12 | Angiotensine-converting enzyme (EC 3.4.15.1) |
| 13 | Tissue kallikrein (EC 3.4.21.35) |
| 14 | Carboxypeptidase A (EC 3.4.17.1) |
| 15 | Cathepsine B (EC 3.4.22.1) |
| 16 | Carboxypeptidase A (EC 3.4.17.1) |
| 17 | Cathepsine B (EC 3.4.22.1) |
| 18 | Carboxylesterase (EC 3.1.1.1) |
| 19 | Carboxylesterase (EC 3.1.1.1) |
| 20 | Phospholipase $A_2$ (EC 3.1.1.4) |
| 21 | Arylesterase (EC 3.1.1.2) |
| 22 | Arylesterase (EC 3.1.1.2) |
| 23 | α/β-glucosidase (EC 3.2.1.20/21) |
| 24 | α/β-galactosidase (EC 3.2.1.22/23) |
| 25 | α/β-mannosidase (EC 3.2.1.24/25) |
| 26 | 3-nucleotidase (EC 3.1.3.6) |
| 27 | α/β-amylase (EC 3.2.1.1/2) |
| 28 | 3'-deoxynucleotidase (EC 3.1.3.34) |
| 29 | 3'-deoxynucleotidase (EC 3.1.3.34) |
| 30 | 3'-deoxynucleotidase (EC 3.1.3.34) |
| 31 | 3'-deoxynucleotidase (EC 3.1.3.34) |

We claim:

1. D-luciferin derivatives which are enzyme substrates, which release luciferin upon reaction with enzyme and which have a formula (I):

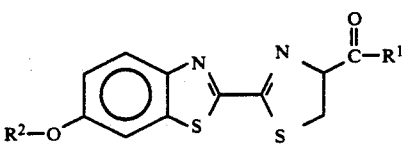

and wherein said luciferin derivative is

D-luciferyl-L-N-alpha-arginine ($R^1$ is L-H-alpha-arginin, $R^2$ is H);

D-luciferyl-L-phenylalanin ($R^1$ is —NH—CH($CH_2C_6H_5$)—COOH, $R^2$ is H);

D-luciferyl-L-methionine ($R^1$ is —NH—CH(($CH_2SCH_3$))—COOH, $R^2$ is H);

D-luciferyl-L-glycine ($R^1$ is —NH—$CH_2$COOH, $R^2$ is H);

D-luciferin-O-sulfate ($R^1$ is OH, $R^2$ is —$SO_2$—OH);

D-luciferin-O-phosphate ($R^1$ is —OH, $R^2$ is —P(O)—$(OH)_2$);

D-luciferin-O-($C^1$)glucose($R^1$ is OH and $R^2$ is glucose); or

D-luciferin-O-($C^1$)galactose ($R^1$ is OH and $R^2$ is galactose).

2. A luciferin derivative according to claim 1 of formula (I), which is

D-luciferyl-L-N-alpha-arginine ($R^1$ is L-H-alpha-arginin, $R^2$ is H);

D-luciferyl-L-phenylalanin ($R^1$ is —NH—CH($CH_2C_6H_5$)—COOH, $R^2$ is H);

D-luciferyl-L-methionine ($R^1$ is —NH—CH(($CH_2SCH_3$))—COOH, $R^2$ is H);

D-luciferyl-L-glycine ($R^1$ is —NH—$CH_2$COOH, $R^2$ is H);

D-luciferin-O-sulfate ($R^1$ is OH, $R^2$ is —$SO_2$—OH); or

D-luciferin-O-phosphate ($R^1$ is —OH, $R^2$ is —P(O)—$(OH)_2$).

3. A luciferin derivative according to claim 1 of formula (I), which is

D-luciferin-O-($C^1$)glucose ($R^1$ is OH and $R^2$ is glucose); or

D-luciferin-O-($C^1$)galactose ($R^1$ is OH and $R^2$ is galactose).

4. In a chemical test wherein a ligand conjugated to an enzyme (enzyme-ligand conjugate) is reacted with its biochemical co-reactant to produce a combination (enzyme-ligand+coreactant) and wherein the enzyme-ligand conjugate, which is either contained in said combination or not, is detected by its reaction with a substrate for such enzyme whereby a measurable species is released and wherein the improvement comprises using as an enzyme substrate a compound which releases luciferin and has a formula (I):

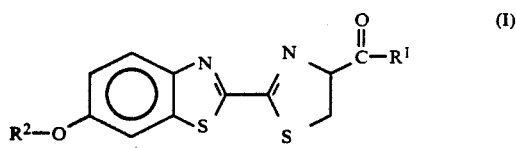

wherein $R^1$ is a hydroxy or amino group; a linear or branched $C_1-C_{20}$ alkoxy or $C_2-C_{20}$ alkenyloxy group; an L-amino acid radical bound by the alpha-amino group; or an oligopeptide radical with up to 10 L-amino acid units, bound by the $\alpha$-amino group of the terminal amino acid unit and $R^2$ is hydrogen atom; a $H_2PO_3-$ or $HSO_3$ group; a linear or branched $C_1-C_{20}$ alkyl or $C_2-C_{20}$ alkenyl group, optionally substituted by one or several phenyl radicals; an aryl group with 6 to 18 carbon atoms; a group of the formula (II):

wherein $R^3$ is a linear or branched $C_1-C_{20}$ alkyl or a $C_2-C_{20}$ alkenyl group optionally substituted by a phenyl radical; or a $C_6-C_{18}$ aryl group; a naturally occurring nucleotide radical with 1 to 3 phosphate groups attached by means of the phosphate group or groups; or a glucosidically attached mono- or disaccharide; which comprises reacting the enzyme conjugate with said luciferin derivative to release luciferin; the released luciferin reacts with the enzyme luciferase of the fire fly *Photinus pyralis* and the amount of light emitted is measured quantitatively and the quantity of the substance to be detected is obtained from the data.

5. A process according to claim 4 for the detection of antigens, haptens or antibodies marked with an enzyme in immunoassays, which comprises releasing luciferin by means of the enzyme conjugate from a luciferin derivative of formula (I):

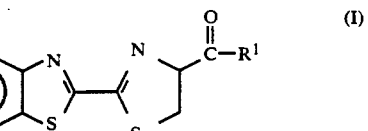

wherein $R^1$ is a hydroxy or amino group; a linear or branched $C_1-C_{20}$ alkoxy or $C_2-C_{20}$ alkenyloxy group; an L-amino acid radical bound by the $\alpha$-amino group; or an oligopeptide radical with up to 10 L-amino acid units, bound by the $\alpha$-amino group of the terminal amino acid unit and $R^2$ is hydrogen atom; a $H_2PO_3-$ or $HSO_3$ group; a linear or branched $C_1-C_{20}$ alkyl or $C_2-C_{20}$ alkenyl group, optionally substituted by one or several phenyl radicals; an aryl group with 6 to 18 C atoms; a group of the formula (II):

wherein $R^3$ is a linear or branched $C_1-C_{20}$ alkyl or a $C_2-C_{20}$ alkenyl group optionally substituted by a phenyl group; or a $C_6-C_{18}$ aryl group; a naturally occurring nucleotide radical with 1 to 3 phosphate groups attached by means of the phosphate group or groups; or a glucosidically attached mono- or disaccharide; which comprises reacting the enzyme conjugate with said luciferin derivative to release luciferin; such that the luciferin released is reacted with the enzyme luciferase of the fire fly *Photinus pyralis*, the amount of light emitted determined quantitatively and the quantity of the antigen, antibody or hapten to be detected is determined from the obtained data.

* * * * *